United States Patent [19]

Galkin

[11] Patent Number: 5,276,726
[45] Date of Patent: Jan. 4, 1994

[54] METHOD OF AND APPARATUS FOR STANDARDIZING AND MONITORING IMAGE QUALITY IN MAMMOGRAPHY

[75] Inventor: Benjamin M. Galkin, Cherry Hill, N.J.

[73] Assignee: Thomas Jefferson University, Philadelphia, Pa.

[21] Appl. No.: 787,849

[22] Filed: Nov. 5, 1991

Related U.S. Application Data

[63] Continuation-in-part of Ser. No. 441,567, Nov. 24, 1989, Pat. No. 5,063,583.

[51] Int. Cl.⁵ ............................................. G01D 18/00
[52] U.S. Cl. .................................. 378/207; 378/173; 378/206
[58] Field of Search ............... 378/169, 172, 183, 182, 378/187, 188, 166, 162, 207, 206, 173

[56] References Cited

U.S. PATENT DOCUMENTS 5,063,583 11/1991 Galkin .................................. 378/207

Primary Examiner—David P. Porta
Assistant Examiner—Don Wong
Attorney, Agent, or Firm—Woodcock Washburn Kurtz Mackiewicz & Norris

[57] ABSTRACT

The invention set forth methods and apparatus for correcting the effect on image quality of a film processor having the steps of shielding a first portion along one edge of a film from x-ray energy and impressing, on the first portion, a first calibrated test pattern having a first calibrated graded stepwise density pattern made from visible light. A first plurality of symbols located adjacent the first pattern to indicate the magnitude of one of the density positions. Impressed along one edge of a control film, a second calibrated test pattern, which includes a second calibrated graded stepwise density pattern made from visible light. A second plurality of symbols are provided adjacent the second pattern to indicate the magnitude of one of the density positions. The performance of the film processor used to develop both films is measured and affected by comparing and noting the symbols associated with those density positions between the first and second test patterns.

32 Claims, 8 Drawing Sheets

METHOD OF AND APPARATUS FOR STANDARDIZING AND MONITORING IMAGE QUALITY IN MAMMOGRAPHY

RELATED APPLICATIONS

The present application is a continuation in part of application Ser. No. 07/441,567 now U.S. Pat. No. 5,063,582, filed on Nov. 24, 1989.

FIELD OF INVENTION

This invention relates generally to the field of radiology, and more specifically to a method and apparatus for standardizing and monitoring image quality in mammography.

BACKGROUND OF THE INVENTION

Radiographic imaging of the body is well known and extremely useful as a diagnostic tool in the medical arts. Radiographic imaging involves positioning a part of a patient to be imaged denoted as a "structure of interest" under an X-ray tube, exposing the structure of interest to an X-ray beam, and recording the X-ray image on an image receptor. The receptor in most instances is a radiographic film disposed in contact with an intensifying screen. The intensifying screen absorbs x-ray radiation and radiates light in proportion to the radiation absorbed. Light emitted by the intensifying screen exposes the film. The film and screen are kept in tight contact during exposure in a film holder or cassette. After exposing the structure of interest, the film is removed from the cassette, may be labeled with the patient's name and other identifying information, and then developed. The use of radiography to image the human female breast is referred to as mammography.

Mammography is today the most important and accurate method for diagnosing breast disease. The diagnostic value of mammograms is highly dependent on image quality which, in turn, depends upon the interplay of several factors: the size, the angle, and elemental composition of the x-ray target, the energy spectrum of the x-ray beam, the type of imaging system, the image processing system, patient radiation dose, etc. Recent studies by the inventor and by others have shown that there is a wide variation in the quality of mammograms being produced at breast imaging facilities in the United States.

Because of the importance of good image quality in mammography a number of regulatory agencies and professional groups have recommended that mammography facilities have an ongoing quality assurance program. One of these professional groups initiated a voluntary accreditation program for mammography centers in 1987. In order to become accredited a mammography facility must, among other things, submit a radiographic image of an inanimate object of intrest known as a breast phantom which contains prescribe artifacts that simulate breast calcifications, tumors and fibrills. Image quality is determined subjectively, i.e., by visual assessment of the phantom image in term of number of artifact seen.

It is well known in the field of radiology to utilize an inanimate object in place of a patient in conducting serial x-ray exposures for calibration or similar purposes. Such an object is called a phantom and in mammography the object is called a breast phantom. Breast phantoms are composed of materials, for example, certain plastics and wax, that simulate the x-ray absorptive characteristics of a human female breast. Small discrete objects are incorporated in a phantom to differentially absorb x-rays in a manner similar to that encountered in a clinical situation in order to produce an image on a receptor such an x-ray film. These objects are usually called artifacts. In some phantoms the artifacts are imbedded in a wax plate that fits into the plastic body of the phantom. In others the artifacts are imbedded in the plastic itself. The artifacts are also sometimes configured to simulate the physiological shape and approximate size of important clinical markers such as tumors, fibrils and calcifications. State of the art breast phantoms usually incorporate nylon fibers of different diameter to simulate fibrils, different size particles of aluminum oxide, calcium carbonate, calcium hydroxyappotite, calcium sulfate, etc. to simulate breast calcifications and cross sections of nylon spheres to simulate tumors. These artifacts are positioned in the phantom in an arbitrary but generally reproducible way and nominal specifications regarding size and sometimes thickness are provided by the vendor. The breast phantom used in the accreditation program consists of a plastic block and a wax insert that contains the artifacts. A radiograph of the insert by itself, that is without plastic block, is provided to the user to demonstrate the location of the artifacts. This image is also intended to demonstrate the maximum number of artifacts that can be visualized in a contact radiograph with essentially no excess scatter. In the accreditation program, the complete breast phantom is radiographed and the scatter causes a loss to the number of artifacts seen. Viewers score image quality on the basis of the number of artifacts seen.

The radiation dose and beam quality used to produce the phantom mammogram is calculated from phantom surface exposure measurements, using solid state detectors, i.e., thermoluminscent dosimetry (TLD). These calculations are typically made by a commercial firm independent of the mammography centers or the accrediting organization, the American College of Radiology.

The diagnostic value of radiographic imaging as described above is dependent on the quality of the radiographic image, which in turn depends on an interplay of several factors. One of the more important of these factors is the process by which the radiographic image is developed. Radiographic images which are made on radiographic films are generally developed in devices called "film processors." Film processors are subject to many variations which are functions of the kind of film processor used to develop the film, the age and quality of the chemicals in the film processor which develop the film, the duration of time the film is processed, and the temperature and pH of the chemicals. Since the diagnostic value of a radiographic image is highly dependent upon the quality of the radiographic image, it is imperative that the film processor be well controlled in order to optimally develop the image. It is also important to minimize fluctuation of processor parameters from film to film.

Processor performance, determined by sensitometry/densitometry measurements of the processor used to develop the radiograph, is generally made in-house by the facility seeking accreditation. A separate thirty day record of processor performance is submitted as part of the documentation for accreditation. However, none of these sensitomery/densitomery meter are directly linked to the phantom image so that the effect of processor performance on the phantom radiograph cannot be taken into account in evaluating image quality.

Data from several thousand mammography facilities participating in this program have now been collected. These data continue to show a wide variation in patient dose and image quality, even amongst facilities that are accredited in the aforementioned fashion.

The same professional group has recently introduced a program to re-accredit mammography centers once every three years and to update accreditation records on a more frequent basis. The subjective method used for image evaluation and the criteria for reaccreditation remains essentially the same.

The inventor of the subject matter herein claimed and disclosed has recognized a need in the art to improve the current method used to evaluate image quality in mammography. Specifically, a need exists for objective image quality standards rather than the subjective type evaluation now being used in the accreditation program. Such image quality standards should be based on physical measurements rather than subjective impressions.

Moreover, processor performance is a critical parameter that needs to be incorporated in any determination of mammographic image quality and the establishment of image quality standards.

A need exists for more frequent independent monitoring of image quality in mammography than once in three years, and that this monitoring too, should incorporate a measurement of the effect of film processing on image quality.

As is known by those with skill in the art, an X-ray image of acceptable diagnostic quality generally comprises an image of the structure of interest as a series of gray levels. Examination of the gray level image indicates whether the structure of interest is healthy, or whether the structure of interest may contain certain diseases such as, for example, cancer.

Since the quality of the radiographic image is highly dependent on the film processor, the film processor must be periodically tested to ensure that the images which are produced have a high diagnostic quality. There are several prior methods currently in use to test film processors. One such method involves the use of a "sensitometer" and a "densitometer." A sensitometer is an instrument which impresses a series of graduated exposures on a photographic material. In these sensitometers, a light source of known luminous intensity is displaced at a fixed distance from an exposure plane and emits radiation of known spectral intensity. The surface of the photographic material is positioned to substantially coincide with the exposure plane.

In the sensitometer, an exposure modulating device is located between a film and the light source. If the exposure modulating device is removed, the entire photosensitive material may be uniformly illuminated. However, the purpose of the exposure modulating device is to alter this condition so that various areas of the photosensitive surface are subjected to a series of different exposures, thereby forming a graded density pattern on the photosensitive surface which is developed as a series of gray levels. This density pattern is a function of the type of film and the action of the processor.

After the film is developed by a film processor with the sensitometric graded density gray scale level pattern imposed thereon, a densitometer is used to measure densities created by the exposure modulating device. In this fashion, the graded density pattern, which may be precalibrated in terms of various parameters such as for example, film speed, base and fog, and contrast, can be used to gauge and evaluate the performance of the film processor.

Various other methods and apparatus have been used to test film processors. Examples of these other methods and apparatus are sensitometric film strips which have been pre-exposed and aged, and are then packaged to be sold commercially. These pre-exposed strips are used in conjunction with a readout device. To check the film processor, one of the strips is developed and inserted into the readout device. When the film is withdrawn, the readout device produces a light signal which indicates the temperature and the condition of the chemicals in the processor. No digital readout is provided and no quantitative indications of the condition of the film processor can be determined.

Methods to check film processors by measuring the pH of the chemicals and the operating temperature of the film processor are also known in the art. It has also been known to use "step wedges" to create a graded pattern on radiographic films. These step wedges are generally constructed of an X-ray absorbing material and are used to determine the effect that the X-rays have on the image quality, but not the effect that the film processor has on the image quality.

The aforementioned prior methods for testing a film processor which develops radiographic images do not satisfy long-felt needs in the art for methods and apparatus to test film processors that are quick, efficient and standardized to particular exposures and film types. The recommended frequency for conducting sensitometric and densitometric tests is daily. However, in the realities of the clinical environment, daily testing of film processors is often not completed.

There are many reasons that daily testing is not always accomplished. Chief among these reasons are that special training and equipment are needed, and additional X-ray film is required. As a result, the diagnostic quality of X-ray images is often severely compromised. Poor film processor performance results in degraded radiographic image quality and could ultimately result in failure to detect diseases. This is particularly devastating, for example, in radiographic images of female breasts called "mammograms" where diagnostic features are often subtle, and early detection of breast cancer is often critical to future survival.

The inventor of the subject matter herein claimed and disclosed has recognized a long-felt need in the art to eliminate repeat densitometric readings of test films to monitor the performance of film processors. There are further long-felt needs in the art to minimize the use of extra test films to monitor processor performance, and also to provide the ability to record the effect of processing on the radiographic image for recall during subsequent examinations. A permanent record of processor monitoring for quality assurance and medicolegal needs is also desired in the art.

SUMMARY OF THE INVENTION

The advantages of the invention are achieved in methods and apparatus for correcting for the effect on image quality of a film processor which develops a radiographic image of a structure of interest on a film having an emulsion. Such methods and apparatus include shielding a first portion of the film along one edge from the x-ray energy used for imaging the structure of interest and impressing a first calibrated test pattern on the first portion of the film. The first pattern includes a first calibrated graded stepwise density pattern having density positions. The density pattern is produced by visible light. A first plurality of symbols is located adjacent the first pattern, wherein each symbol indicates the magnitude of one of the density positions. A control film of similar emulsion as the emulsion of the image film is provided and impressed with a second calibrated test pattern along one edge. The second pattern includes a second calibrated graded stepwise density pattern having density positions, which pattern is also produced by visible light. A second plurality of symbols is located adjacent the second pattern, wherein each symbol indicates the magnitude of one of the density positions. The intensity and spectrum of the visible light used for impressing the first and second patterns is adjustable. The film is processed in a film processor to develop the first pattern and the radiographic image of the structure of interest. The control film is processed to develop the second pattern. The performance of the film processor used to develop the film is measured by comparing and noting the symbols associated with those density positions between the first and second patterns which match. Physical parameters of selected portions of the developed image of the structure of interest are measured, such parameters modulating image quality. These parameter measurement are corrected for the effect of film processor performance by adjusting their values according to the optical density values at the match positions of the first and second patterns.

BRIEF DESCRIPTION OF THE DRAWINGS

The present invention will be better understood, and its numerous objects and advantages will become apparent to those skilled in the art by reference to the following detailed description of the invention when taken in conjunction with the following drawings, in which.

DETAILED DESCRIPTION OF PREFERRED EMBODIMENTS

Figure 1A:
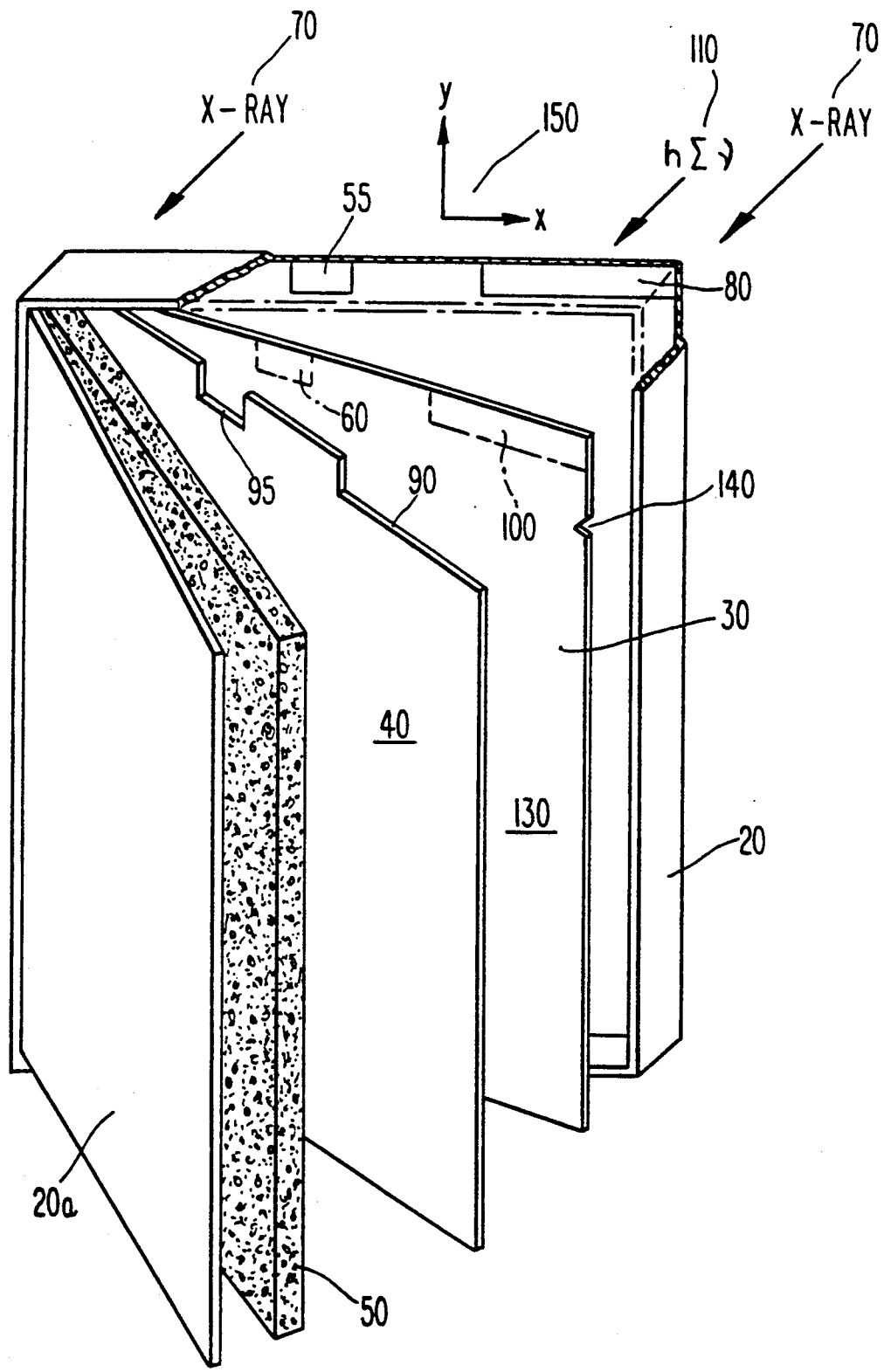
FIGS. 1A and 1B are isometric views of cassettes for holding radiographic films.

Referring now to the drawings wherein like reference numerals refer to like elements, in FIG. 1A a cassette holder having a front cover 20 and back cover 20a provides a housing for the film 30. The film 30 is generally a type of radiographic imaging film. In preferred embodiments, a silver halide emulsion coats a first side of the film 30 and absorbs radiation to form an image of a structure of interest on film 30.

Means for intensifying X-rays 40 is provided to the cassette. Intensifying means 40 is generally a screen that is placed in cooperative relationship with radiographic film 30 to intensify the X-rays, shown at 70, which carry information about the structure of interest. Intensifying screen 40 fluoresces when X-rays 70 impinge on it such that the fluorescent radiation forms an image of the structure of interest on film 30.

In preferred embodiments, film 30 is a single emulsion film for use in mammography. Thus, the structure of interest can be either a human breast or a breast phantom. Since a single emulsion film is used in mammography, only one intensifying screen 40 is provided to the cassette. However, in other radiographic imaging techniques where double emulsion films are typically used, two intensifying screens are provided to the cassette. In describing the invention hereinafter, reference will be made to single emulsion radiographic films for use in mammography wherein the structure of interest is a human breast or breast phantom and the cassettes therefore have a single intensifying screen.

In further preferred embodiments, a pressure pad 50 is placed in the cassette in cooperative relation with intensifying screen 40 so that when the cassette is closed, intensifying screen 40 fits snugly against film 30 during X-ray imaging of the breast or breast phantom. Means 55 for allowing codable information to identify the patient or breast of phantom to be impressed on film 30 is integrally formed on front cover 20. Codable means 55 provides for an area 60 on film 30 wherein identifying information of the patient or breast phantom can be impressed on film 30. Codable means 55 blocks X-rays so that coding area 60 is not impressed with a radiographic image during imaging of the breast or breast phantom. Preferably, the identifying information is impressed photographically on coding area 60 after the breast or breast phantom is imaged.

Similarly, means 80 for blocking X-rays 70 is integrally mounted on front side 20 and interfaced with a first portion 100 of film 30 to block X-ray energy from reaching the first portion 100 of film 30. In this fashion after X-rays 70 have irradiated film 30, the silver halide emulsion which exists on the first portion 100 of the film has not been irradiated and remains pristine. Furthermore, intensifying screen 40 does not fluoresce radiation onto first portion 100 since X-rays are blocked from reaching screen 40 in an area corresponding to the first portion 100. Thus, other information may be impressed on the first portion 100 of the film 30, rather than the information about the breast or breast phantom which has been carried by X-rays 70 to a second portion 130 of film 30.

Since the first portion 100 of film 30 and coding area 60 are not to be impressed with radiographic images of the breast or breast phantom, the intensifying screen 40 is cut out at 90 and 95 corresponding to areas on film 30 substantially equal to the area of the first portion 100 and coding area 60 respectively. Since it is desired that no fluorescent energy reaches the first portion 100 of film 30 and area 60, cutouts 90 and 95 in intensifying screen 40 are provided to ensure that no florescent energy reaches the first portion of the film 100 and area 60.

Figure 1B:
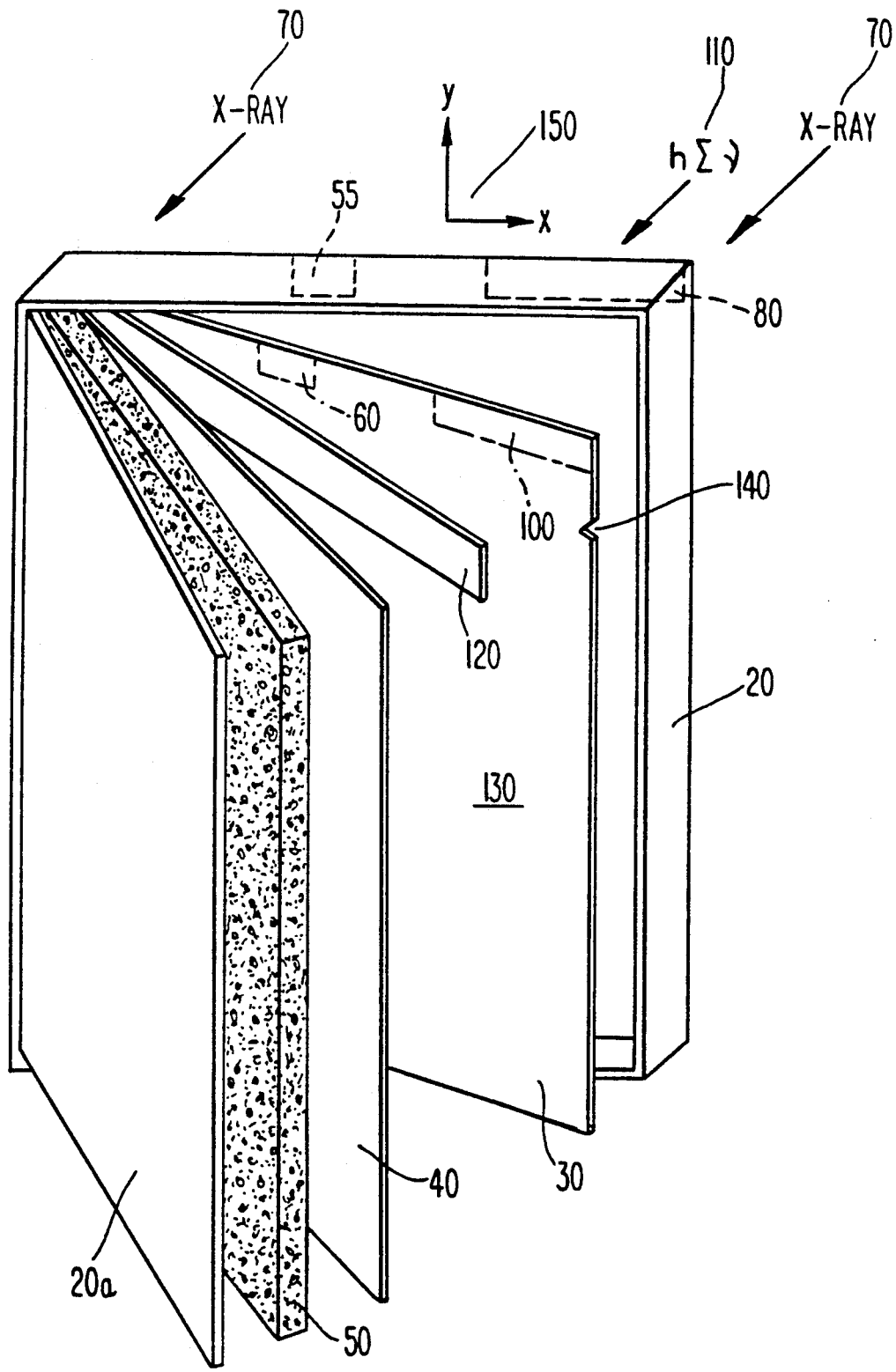

Other means may be provided to the cassette to ensure that area 60 and first portion 100 are not impressed with radiographic images during imaging of the structure of interest. Referring to FIG. 1B, light blocking means 120 is provided to the cassette disposed between intensifying screen 40 and film 30. Light blocking means 120 is generally a strip of opaque material having approximately the same extent in the X and Y directions as area 60 and first portion 100. Light blocking means 120 prevents florescent energy from reaching area 60 and first portion 100, or more specifically, the space on film 30 corresponding to the area of light blocking means 120.

In yet further preferred embodiments, intensifying screen 40 could simply be made smaller than film 30 so that area 60 and first portion 100 are not illuminated with florescent energy from the screen. Alternatively, an X-ray blocker could be integrally formed in front cover 20 to prevent X-rays 70 from reaching areas on screen 40 corresponding to area 60 and first portion 100. An X-ray blocker of this sort preferably comprises a thin sheet of lead which absorbs the X-rays.

The first portion 100 of film 30 is adapted to receive a graded density test pattern which acts as a test means to determine the performance of the film processor that develops the mammogram on second portion 130 of film 30. The graded density pattern is impressed on the first portion 100 of film 30 by a standard sensitometric technique. After the radiographic image of the structure of interest has been impressed on second portion 130, film 30 is removed from the cassette in a darkroom so that the graded density pattern can be impressed on first portion 100. Similarly, identifying information for the structure of interest is photographically impressed on coding area 60 after film 30 has been removed from the cassette. During impression of the graded density test pattern on first portion 100, light having a known spectral content, shown generally at 110, irradiates the film on first portion 100. The light 110 is multifrequency, having energy equal to $h\Sigma\nu$ signifying radiant energy associated with a range of frequencies. The light 110 is generally emitted from a sensitometer having first been modulated by an exposure modulating device (not shown) and therefore, has a known spectral intensity corresponding to the various frequencies in light 110. A graded density test pattern is thus impressed on film 30 in first portion 100. Alternatively, the graded density pattern can be impressed on first portion 100 before imaging of the structure of interest.

In still further preferred embodiments of the cassette provided in accordance with the present invention, the X-ray blocking means 80 and codable means 55 are comprised of a material which absorbs X-rays, thereby preventing the X-rays from reaching intensifying screen 40. Various types of polymer plastics, absorbing foils, or other radiant energy absorbers may thus be used to form X-ray blocking means 80 and codable means 55. Similarly, light blocking means 120 is also constructed of a material which can absorb light comprising multifrequencies.

A graded density test pattern is impressed on the first portion 100 of film 30 by light of known spectral content 110. Thus, film 30 will have essentially two types of useful images impressed thereon. The first image is the standard radiographic image of a structure of interest on the second portion 130 of film 30 called a mammogram. The other image is formed on the first portion 100 of film 30, and is a graded density pattern which is used to test and evaluate the performance of the film processor.

The graded density test pattern is generally a sensitometric image whose development is highly dependent upon the parameters which affect the film processor. Thus, it is possible to use the graded density test pattern to evaluate the film processor's performance independently of other factors that effect the image of the structure of interest, and to ensure that the mammogram formed on the second portion 130 of film 30 is a high quality image that is useful for diagnostic purposes.

It is generally desired to provide means 140 interfaced with film 30 to identify film type. There are many types of radiographic films which can generally be used to form radiographic images. Depending on the type of film used, the film processor will develop the film and produce images whose gray scale is also dependent on film type corresponding to particular radiographic needs.

In yet further preferred embodiments, means 140 for identifying film type is simply a "notch" which is cut out of film 30, and placed in a preferred orientation on film 30. A cartesian coordinate system 150 indicates that notch 140 is oriented along the long edge of film 30. In other preferred embodiments, notch 140 could be oriented along the narrow edge of the film. As is conventional, when film 30 is held in the right hand and notch 140 is in the upper right hand corner, the emulsion side of film 30 faces the individual holding film 30. There may be a single notch, or a series of notches of various shapes cut into film 30 to indicate the particular film type.

Figure 2A:
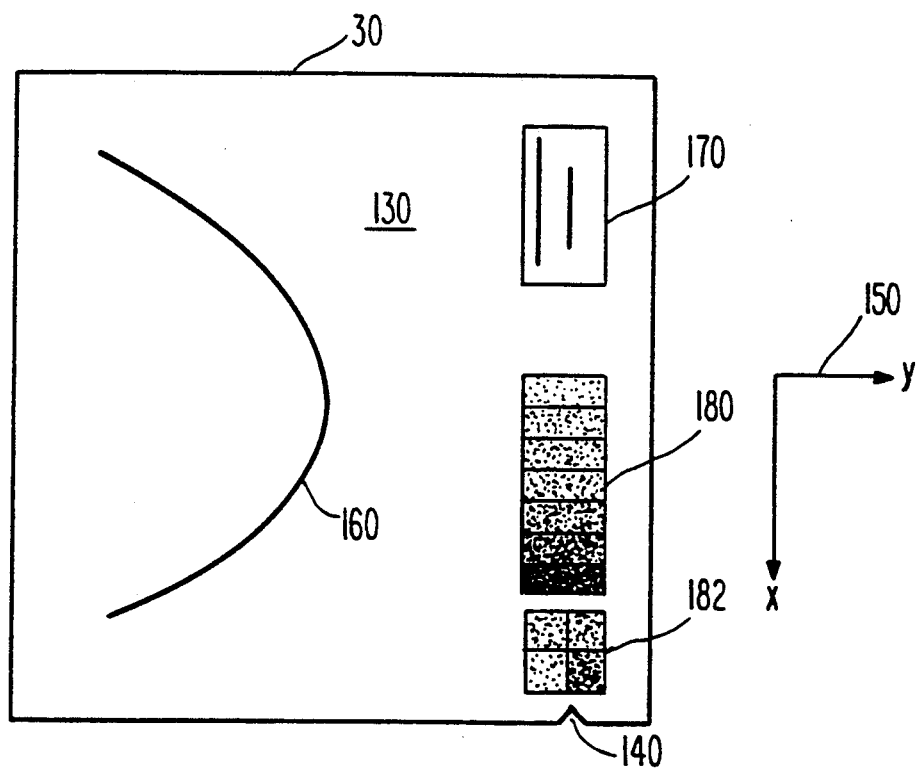
FIGS. 2A, 2B and 2C are schematics of radiographic films in accordance with the present invention.

Referring to FIG. 2A, a radiographic image, herein a mammogram, is shown at 160. As is known by those with skill in the art, female breasts are subject to a particularly devastating form of cancer which, if detected early, may be curable with a high success rate. Thus, high quality mammograms are desired in the radiographic imaging art to allow radiological physicians and professionals to make early and accurate diagnoses of breast cancer.

The film 30 generally comprises an exposable area which is coated with a silver halide emulsion. The exposable area, corresponding to first portion 100, area 60 and second portion 130 in FIGS. 1A and 1B, has impressed thereon various images including mammogram 160, coding area 170 for identifying the patient, and test means 180 and 182 which are generally a graded density test pattern and a contrast pattern that have been sensitometrically produced. In preferred embodiments, coding means 170 may be photographically produced, but it could simply be mechanically attached to the exposable area of film 30. Notch 140 indicates the film type, and is oriented in a preferred direction along an edge of the film.

Figure 2B:
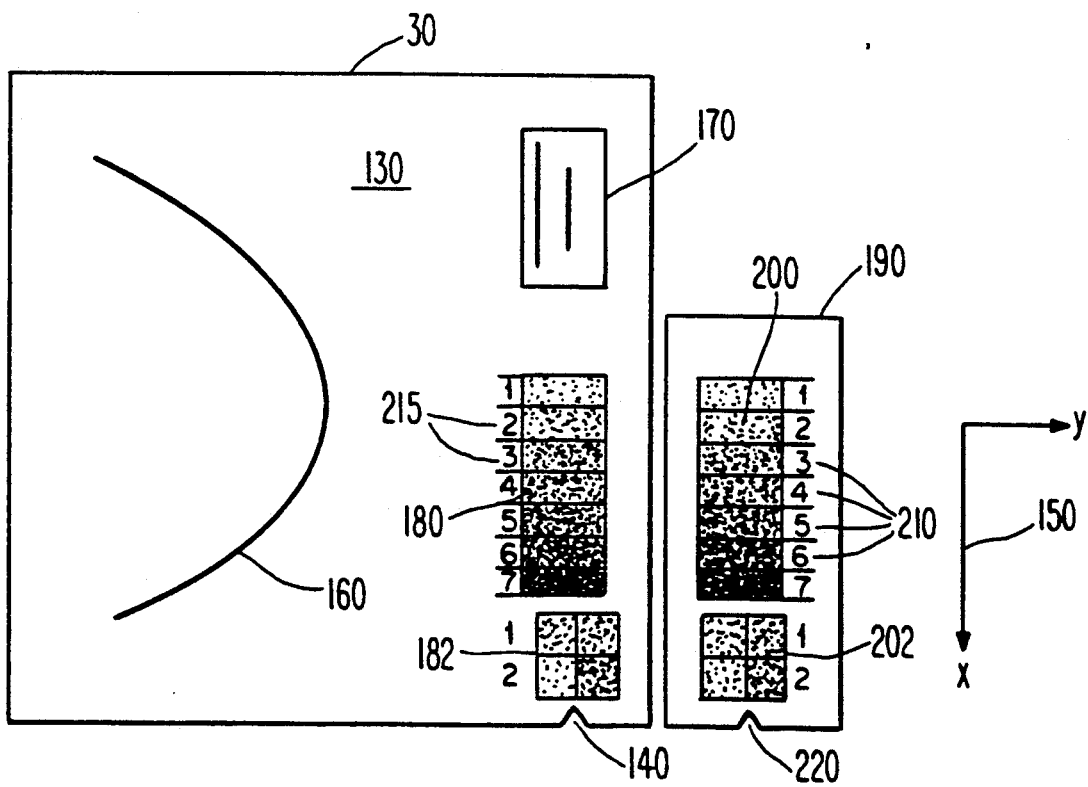

As is illustrated in FIGS. 2A and 2B, graded density test pattern 180 in preferred embodiments is a series of gray levels impressed on film 30. Referring to FIG. 2B, a control film 190 is placed in a proximate position to film 30 so that a control density pattern 200 and a control contrast pattern 202 impressed on control film 190 can be compared to graded density test pattern 180 and contrast pattern 182 impressed on film 30. In preferred embodiments, control density pattern 200 is also a graded density pattern.

In accordance with the present invention, control density pattern 200 impressed on control film 190 is held in position while film 30 having graded density test pattern 180 and mammogram 160 imposed thereon is placed in a proximate position to control film 190 so that graded density test pattern 180 and control density pattern 200 can be visually compared. Variations from accepted norms of graded density test pattern 180 as compared to control pattern 200 may then be visually noted by comparing step markers 210 on control film 190 to step markers 215 on film 30, thereby indicating the quality by which the film processor has developed mammogram 160 on film 30. Step markers 210 and 215 correspond to the various gray levels in control density pattern 200 and graded density test pattern 180, respectively.

Markers 210 provide an indication of what parameters have been measured, for example, film speed, base and fog, and contrast. Control density pattern 200 is calibrated to provide a gray scale indication of a film processor that is considered to be performing optimally in developing radiographic images. By lining up the gray levels on test pattern 180 to the corresponding gray levels on control pattern 200, the difference between step markers 215 and step markers 210 can be noted. Step markers 215 and 210 may be numbers corresponding to gray levels, or generally any type of standardized symbols that provide an indication of the magnitude of the gray levels. The difference between the step markers 215 and 210 after the gray levels on graded density test pattern 180 and control density pattern 200 have been matched provides an indication of how the film processor is performing, and therefore the diagnostic quality of mammogram 160. In a similar manner, the contrast patterns 182 and 202 can be compared.

Radiographic films provided in accordance with the present invention eliminate the need for complex, frequent densitometric tests of film processors. Thus radiographic films and control films provided in accordance with the present invention eliminate costly, independent densitometric tests of radiographic films to determine film processor performance, and greatly streamline the testing process for the film processor. No inaccuracies in determining performance of film processors is engendered through the use of methods and apparatus provided in accordance with the present invention because a human eye can detect differences in density of at least 0.05. This is well within the accepted requirements for analyzing sensitometric graded density patterns to determine film processor efficiency and performance.

In accordance with the present invention, notch 220 is physically cut from control film 190 to determine the control film type. By comparing notch 220 with notch 140, the radiologist can ensure that the same type of film which is used in constructing mammogram 160 is used to provide the control density pattern 200.

Methods and apparatus provided in accordance with the present invention are generally useful for both dedicated and non-dedicated film processors. A "dedicated" film processor is one that is used exclusively for developing a single type of radiographic emulsion that such as used in mammography. However, most film processors are "non-dedicated" because they are used to develop a number of different kinds of radiographic emulsion including mammograms. Since control film 190 is precalibrated for a particular emulsion to represent an optimal film processor, it is useful in determining the performance of both dedicated and non-dedicated film processors. Thus, methods and apparatus for testing both dedicated and non-dedicated film processors provided in accordance with the present invention solve long-felt needs in the art for efficient and cost-effective tests to ensure that mammograms and other radiographic images are of the highest quality for diagnostic purposes. These needs have not been satisfied by methods and apparatus which have existed prior to the invention herein claimed and disclosed.

Figure 2C:
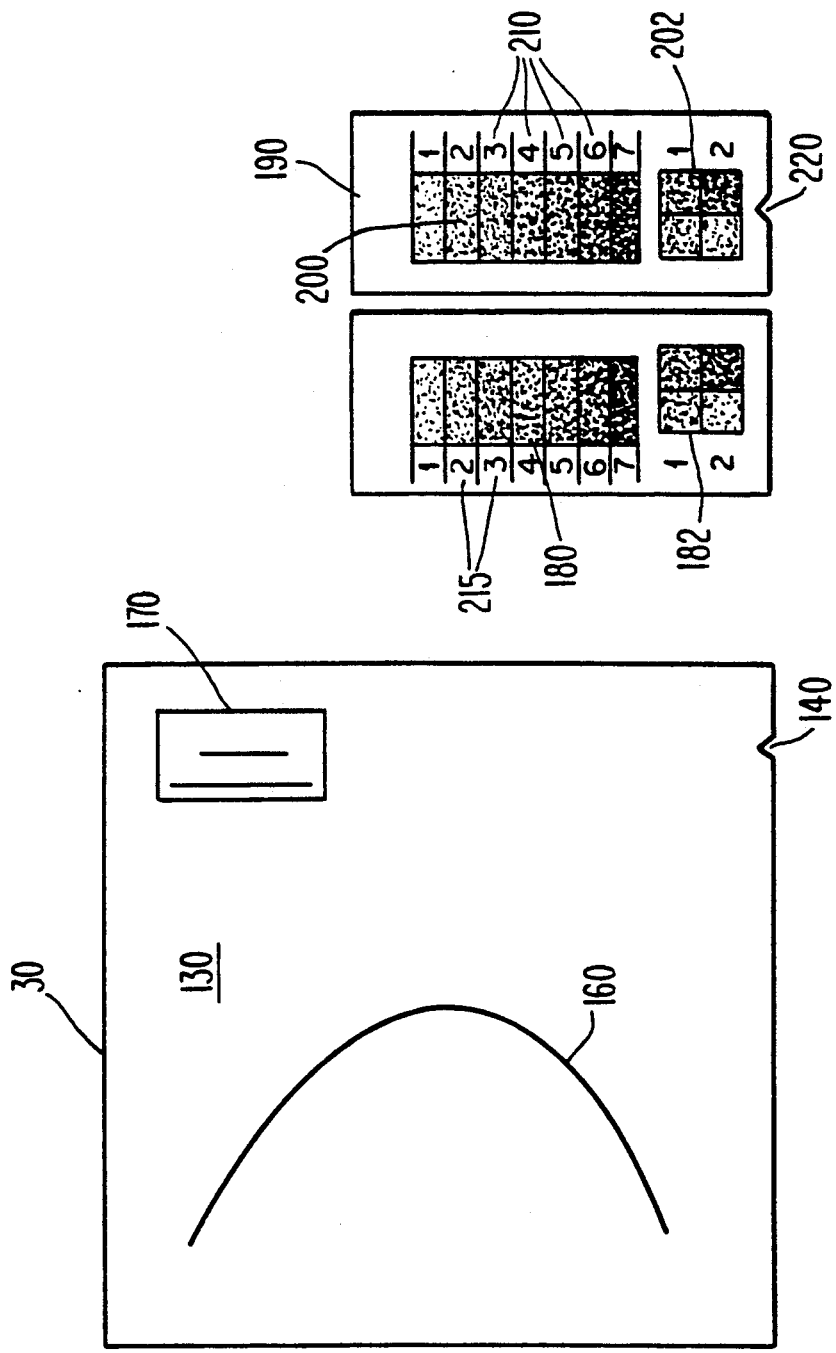

It is also within the scope of the present invention for the film containing the structure of interest, the first density pattern and the second density pattern to be formed on separate films, as shown in FIG. 2C. In such a situation, each film will have an emulsion, wherein it is preferred for all emulsions to be identical. The density patterns are formed in a manner identical to that described above. It is noted however, that best results can be obtained if the image film and the test film are processed either simultaneously or close in, time in the same processor. It may also be desirable to process the image film, the test film and the control film and the image film simultaneously. It may still further be desireable for the multiple films to have identifying information impressed thereon.

In other words, a series of films may be used for determining the effect on image quality of changes in film fog, speed or contrast resulting from changes in the performance of a film processor. In such an embodiment of the invention, the series of films will include an imaging film, having a first emulsion, which has been exposed to x-rays to image a structure of interest. A test film, of a second emulsion, having a first calibrated test pattern impressed thereon, preferably by a sensitometer, is also included in the series of films. The first pattern includes a first calibrated graded stepwise density pattern having density positions. The density pattern is produced by visible light and includes a first plurality of symbols, located adjacent the first calibrated graded density pattern. Each symbol indicates the magnitude of one of the density positions. The imaging film and the test film are developed/processed in the subject film processor. A control film, of a third emulsion, contains a second calibrated density pattern produced by visible light and a second plurality of symbols located adjacent the second pattern. Each symbol indicates the magnitude of a portion of the calibrated graded density pattern. In one situation, the structure of interest can include calibrated test objects for measuring film quality. Such calibrated test objects include objects that are calibrated in terms of size, shape, thickness and composition. It is also preferred for the series of films to have at least one notch cut in the edge of the imaging film and in the edge of the control film. The notch identifying the type of emulsion contained on the imaging and control films. It may be desirable for the imaging film and the test film to be processed sequentially in the same film processor. It may also be desirable for the imaging film and control film to include identification information.

Heretofore, in mammography accreditation programs, such as those presently being conducted, image quality is determined subjectively. A viewer counts and scores image quality on the basis of the number of artifacts visualized in a radiographic image of a standardized phantom. No objective measurements of important image quality parameters such as contrast, density, resolution, or density gradient are made of the artifacts and no comparison is made against measured physical standards for these variables. The above described embodiments adapt well to resolving the image quality standardization problem.

The standardization problem is resolved by first forming a film and control film as previously described. i.e. with the density and/or contrast patterns impressed thereon. Thereafter such films are processed in a film processor to develop the films. The performance of the film processor is measured by comparing the density positions between the first calibrated test pattern on the film and the second calibrated test pattern on the control film and determining which positions match. Portions of the image of the structure of interest are adjusted optically in size and the adjusted image is converted to an electrical signal using a video camera. The physical parameters of the adjusted image of the structure of interest are measured from the electrical signal and corrected for the effect of the film processor by adjusting the measurements of the parameters in relation to the optical density values at the match positions of the first and second calibrated test patterns.

Figure 3:
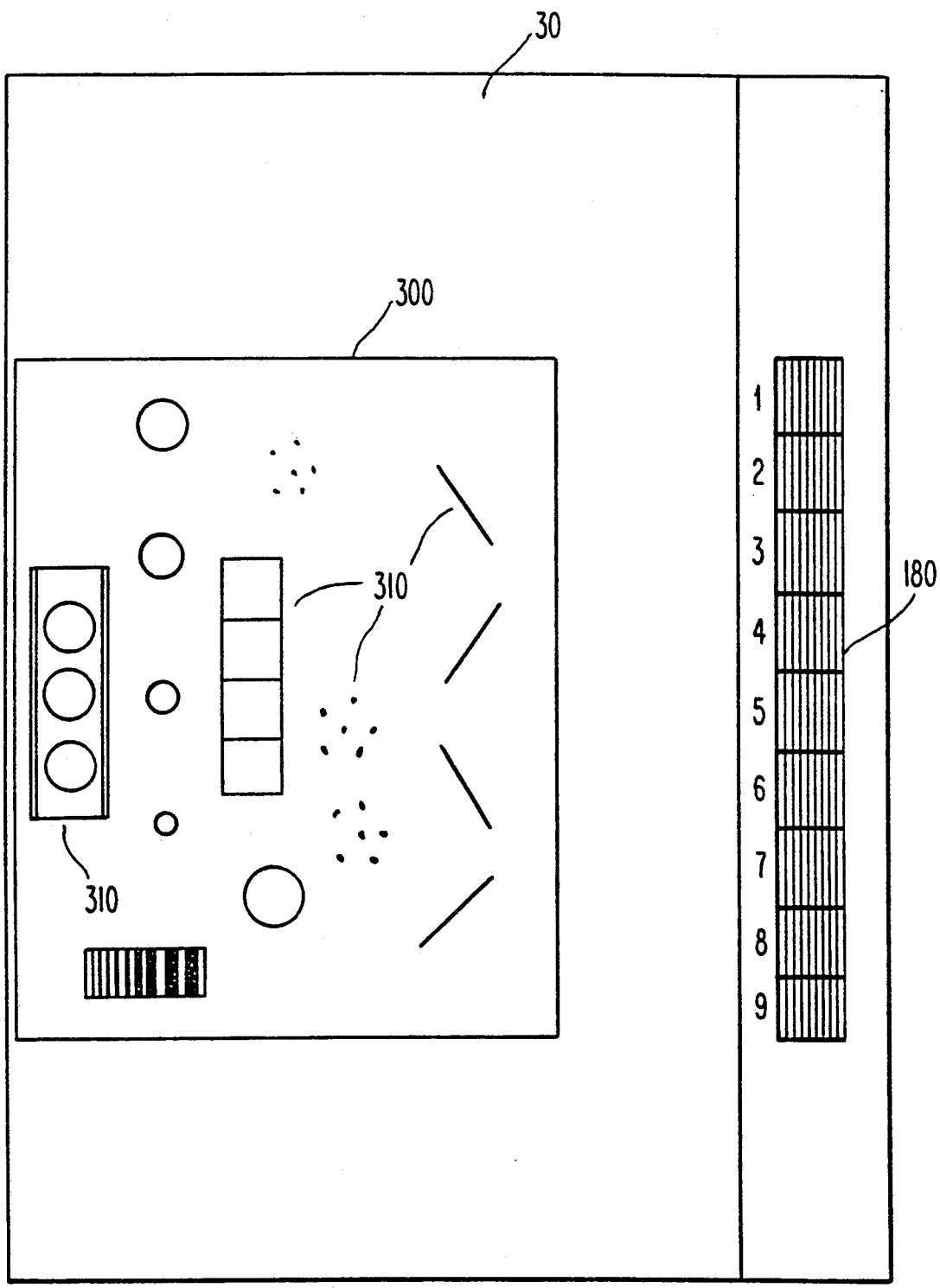
FIG. 3 is an exposed and processed x-ray image of a breast phantom containing a number of artifacts for use in the present invention.
Figure 4:
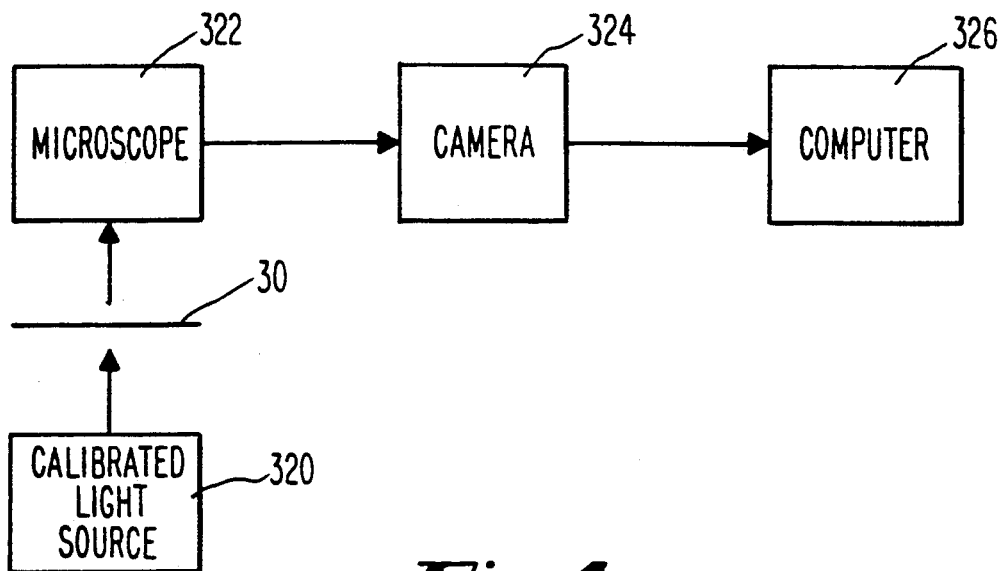
FIG. 4 is a block diagram showing a quality assurance system constructed in accordance with the present invention.
Figure 5:
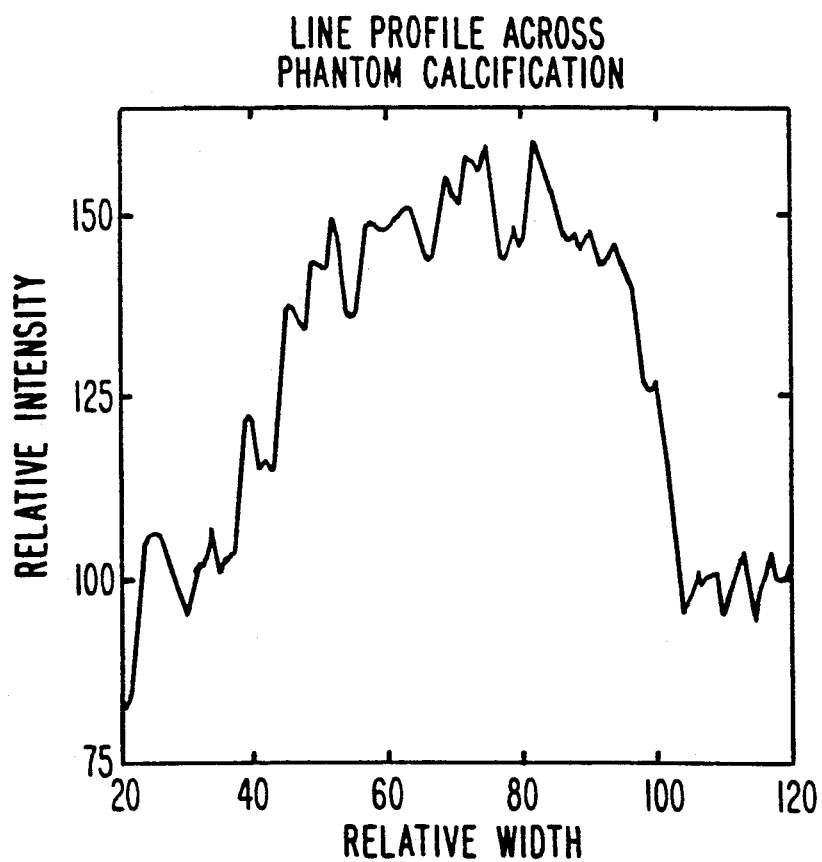
FIG. 5 is a transmitted light intensity graph showing a line profile across one of the artifacts depicted in FIG. 3.

Such a method can be more clearly understood by reference to FIGS. 3-5. In FIG. 3, an x-ray image of a breast phantom 300 has been formed on film 30 together with a light induced image of graded density pattern 180. As will be appreciated, phantom 300 contains several artifacts 310, which as explained previously are intended to simulate various physiological features of the human breast. One of those artifacts is a calcification. Since such artifacts contain relatively tiny features, that portion of the phantom is magnified. The film also contains images of a contrast pattern 311 and a resolution pattern 312 produced by the x-ray beam. Radiation dose can be measured using separate solid state or film dosimeters 313 exposed while obtaining the radiograph of the phantom. It is noted that FIG. 3 is a schematic representation of an x-ray image of a breast phantom and of a sensitometric calibrated density pattern, wherein the numbers or symbols represent different density positions.

As shown in FIG. 4, film 30 is placed over a calibrated light source. The particular artifact is illuminated by light source 320 which emits light of a known intensity, spectrum and spatial orientation. Such spatial orientation can be determined from a calibration process, wherein a blank is placed over the emitting surface of source 320. Light intensity is then measured so that when an image is placed on the source, corrections can be made for any non-uniformities in intensity that are present. It is noted that while a uniform light source is preferred, a calibrated light source can be utilized. Microscope 322, which in the preferred embodiment is a binocular dissecting microscope, receives the light passing through film 30 and magnifies the structure of interest forming a magnified image. It is noted that artifact size can be determined using microscope 322, provided the microscope contains internal measurement features, such as a reticule. It is also noted that for larger artifacts, magnification may not be necessary, however, calibration of the light source is still required. The magnified image is directed in any known manner onto video camera 324, which in the preferred embodiment exhibits a logarithmic response.

Camera 324 converts the magnified image into an electrical signal, i.e. digitizes the image, which is provided to computer 326 for storage and/or manipulation. In the preferred embodiment, computer 326 includes a display for displaying the electrical signal. Such a displayed signal is depicted in FIG. 5. From this signal physical parameters can be measured, which parameters are thereafter corrected in relation to a comparison between the density patterns 180 and 200. It is noted that in the preferred embodiment, camera 324 also provides a video monitor. If electronic markers are displayed on the monitor, artifact size can be determined.

Figure 8:
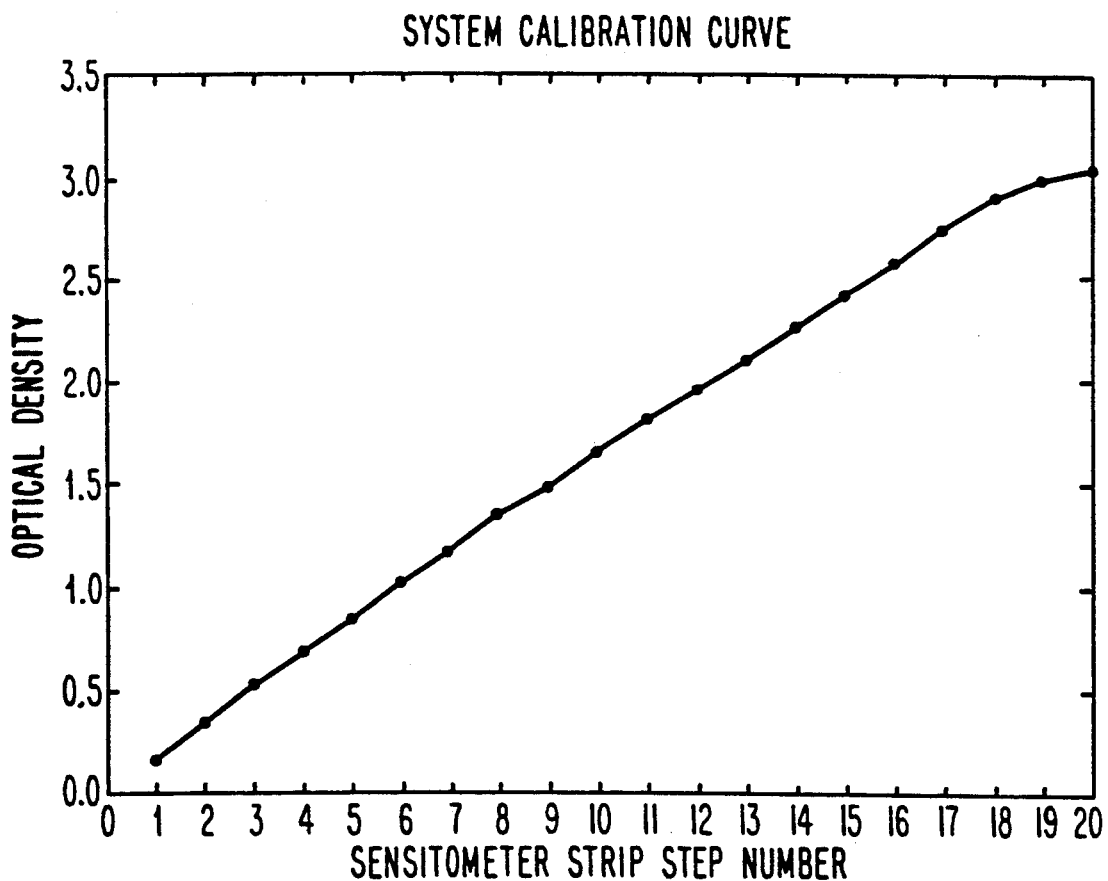
FIG. 8 is a graph of optical density versus sensitometer strip step number.

In the preferred embodiment, camera 324 is an ITM Data Vision Model 250 SOFCAM camera. This camera is preferred because it exhibits a logarithmic response with relation to transmitted light. Such a logarithmic response converts to a linear relationship as shown in FIG. 8.

In the preferred embodiment the graded density patterns are provided with symbols. In such a case, the comparison of the density positions between the test patterns involves noting the symbols associated with those positions on the control film which match.

It is noted that the image quality of a radiographic imaging film can be more accurately evaluated when one utilizes a phantom image, formed in accordance with the above methods or by using apparatus of the present invention, in conjunction with the information relating to the corrections made to the physical parameters to account for the effect of the film processor. Such information can be stored in any known storage device such as an electronic memory, if such information is in the form of an electrical signal or on a hard copy if such information has been printed.

It is also possible to correct for the effect on image quality of a film processor which develops a radiographic image of a structure of interest by taking a film produced in accordance with the above described methods, by measuring the performance of the film processor by comparing and noting the symbols associated with those density positions between the first calibrated test pattern on the film and the second calibrated test pattern on the control film which match, by measuring physical parameters of selected portions of the developed image of the structure of interest, wherein the parameters define image quality and by correcting for the effect of film processor performance on image quality by adjusting the values of the measured physical parameters according to the optical density values at the match positions of the first and second calibrated test patterns.

To obtain the objective data needed to standardize image quality in mammography, the artifacts in the phantom are carefully calibrated according to size, shape, thickness and chemical composition. Sections of the breast phantom image that show the artifacts and other selected portions of the radiograph are measured using the magnification video analysis. Sections of the film containing the image of one or more of the artifacts are optically magnified by a predetermined amount and the magnified images are subjected to video image analysis. The light intensity, light spectra light uniformity used to illuminate the portion of the film being examined is carefully measured and controlled. The following image parameters are measured: absolute and relative optical density of the images of the artifacts; optical density profiles across the artifacts, line density across high contrast and a low contrast resolution patterns, radiation dose from density measurements of the film, processor performance by density measurements of the graded density pattern.

Figure 6:
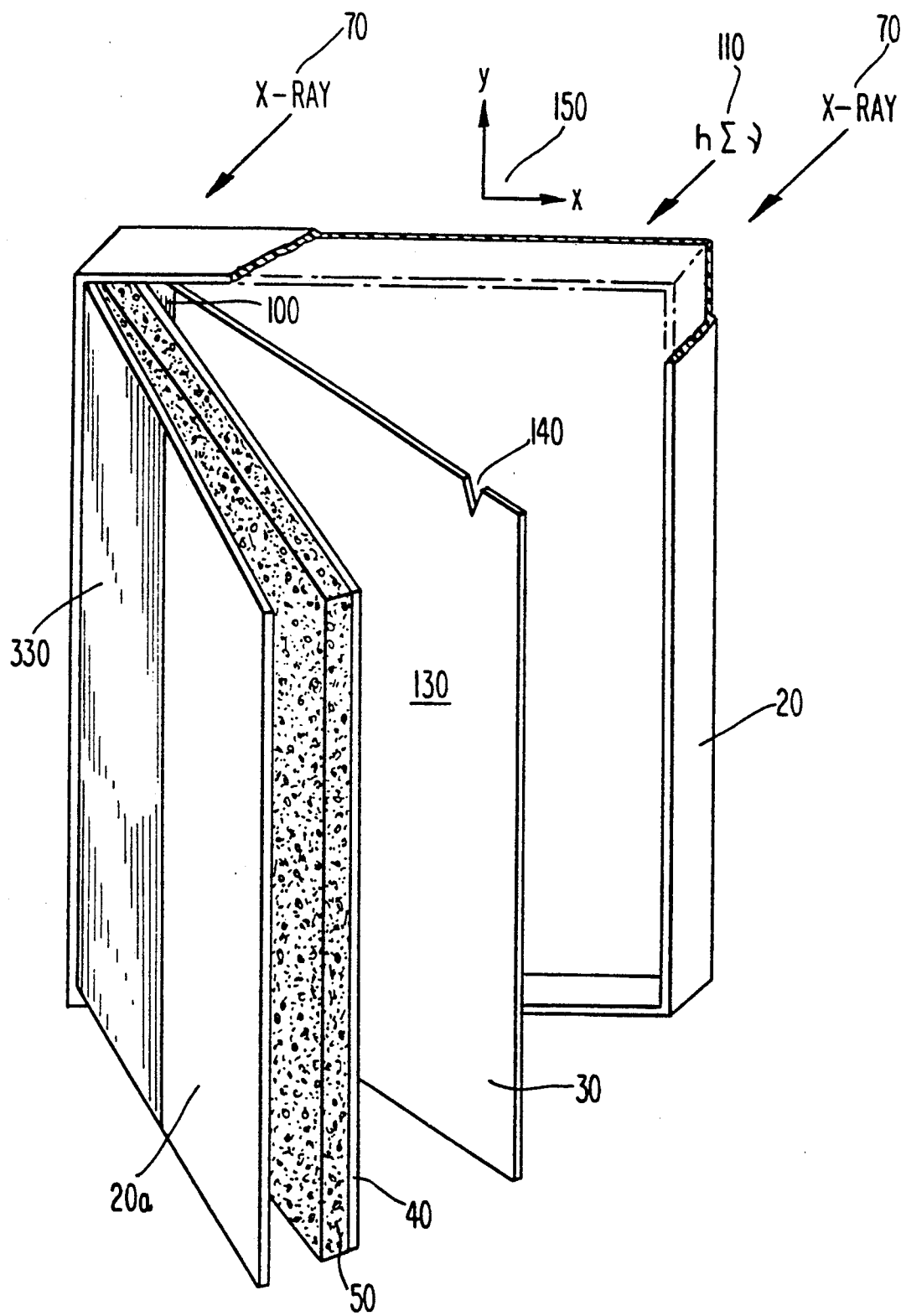
FIG. 6 is an isometric view of cassette constructed in accordance with the invention for holding radiographic films.

Referring now to FIG. 6, there is shown an alternative cassette, wherein an x-ray impervious shield 330 formed for example from lead is positioned along one edge of cover 20a. Such a shield is used to prevent x-rays from causing the exposure of an edge of film 30. It is preferred to impress the graded density pattern in this area. In the preferred embodiment, shield 330 is formed on the inner surface of cover 20a. However, it is also within the scope of the invention for shield 330 to be formed within cover 20a or on the surface of cover 20a.

Figure 7:
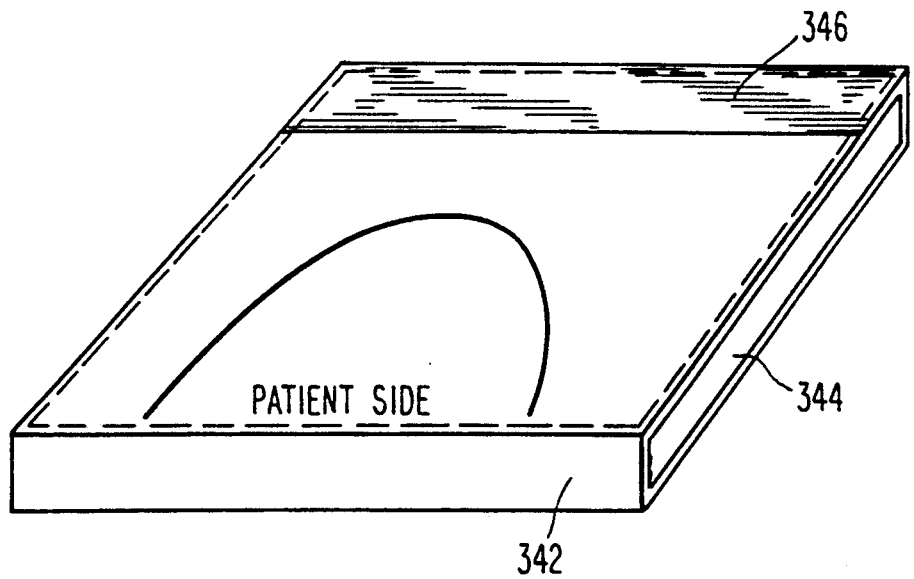
FIG. 7 is an isometric view of a cassette holder constructed in accordance with the invention.

Referring now to FIG. 7, an alternative method is shown for providing the desired shielding to a portion of film 30 along one edge. In this embodiment there is shown a cassette holder 342 which is attached to an x-ray unit. Holder 342 is substantially hollow presenting an opening 344, which is sized for insertion of a cassette such as that shown in FIGS. 1A, 1B and 6. An x-ray impervious shield 346 is formed along one edge of holder 342. When a cassette is inserted, x-rays will be prevented from causing the exposure of film 30 along an edge.

While the above summary and attached drawings describe the invention as used in film mammography, the invention is also applicable for xeromammography and other radiographic imaging procedures.

While the invention has been described and illustrated with reference to specific embodiments, those skilled in the art will recognize that modification and variations may be made without departing from the principles of the invention as described herein above and set forth in following claims.

What is claimed is:

1. A method of correcting measured physical parameters of a radiographic image of a structure of interest for the effect on image quality of a film processor which develops said radiographic image on a film having an emulsion, comprising the steps of:

shielding a first portion of the film along one edge of the film from x-ray energy used for imaging of the structure of interest;

impressing a first calibrated test pattern on the first portion of the film, said first pattern comprising a first calibrated graded stepwise density pattern having density positions, said density pattern produced by visible light of controlled intensity and spectrum;

providing a control film of similar emulsion as the emulsion of said film;

impressing a second calibrated test pattern along one edge of said control film said second calibrated test pattern comprising a second calibrated graded stepwise density pattern having density positions, said density pattern produced by visible light of controlled intensity and spectrum, wherein the intensity and spectrum of the visible light used for impressing said first calibrated test pattern and second calibrated test pattern are similar;

processing said film in a film processor to develop the first calibrated test pattern on said first portion of said film and the radiographic image of the structure of interest on another portion of the film;

processing said control film to develop the second calibrated test pattern;

measuring the performance of the film processor used to develop the film by comparing the density positions between the first calibrated test pattern on the film and the second calibrated test pattern on the control film which match;

optically adjusting the size of the image of the structure of interest forming an adjusted image, wherein the light source used is corrected for variations in light intensity;

converting said adjusted image to an electrical signal;

measuring physical parameters of the adjusted image of the structure of interest from said electrical signal; and correcting the measured physical parameters for the effect of the film processor by adjusting the measured values of said parameters in relation to the optical density values at the match positions of the first and second calibrated test patterns.

2. The method of claim 1, further comprising the step of impressing a first plurality of symbols, located adjacent said first calibrated graded density pattern, wherein each symbol indicates the magnitude of one of said density positions.

3. The method of claim 2, further comprising the step of impressing a second plurality of symbols, located adjacent second calibrated graded density pattern, wherein each symbol indicates the magnitude of one of said density positions.

4. The method of claim 3, wherein said step of comprising the density positions between the first and second calibrated test patterns comprises the step of noting the symbols associated with those positions on the control film which match.

5. The method of claim 1, further comprising the step of:

storing information relating to the adjustments made to the measured values of said physical parameters to account for the effect of the film processor.

6. Apparatus for correcting measured physical parameters of a radiographic image of a structure of interest for the effect on image quality of a film processor which develops said radiographic image, said apparatus comprising:

a film having an image portion for impressing said radiographic image thereon and having a first portion of the film along one edge having impressed thereon a first calibrated test pattern, said first pattern comprising a first calibrated graded stepwise density pattern having density positions, said density pattern having been produced by visible light of controlled intensity and spectrum;

a control film having impressed thereon a second calibrated test pattern along one edge of said control film said second calibrated test pattern comprising a second calibrated graded stepwise density pattern having density positions, said density pattern having been produced by visible light of controlled intensity and spectrum, wherein the intensity and spectrum of the visible light used for impressing said first calibrated test pattern and second calibrated test pattern are generally similar, wherein said first and second density patterns can be compared;

a converter for converting said image of said structure of interest to an electrical signal; and a computer, connected to receive said electrical signal, for measuring physical parameters of the image of the structure of interest from said electrical signal and for correcting the measured physical parameters for the effect of the film processor by adjusting measurements of said parameters in relation to the optical density values at the match positions of the first and second calibrated test patterns.

7. The apparatus of claim 6, further comprising a magnifier for optically magnifying a portion of said image of said structure of interest thereby forming a magnified image, wherein said magnified image is converted by said converter.

8. The apparatus of claim 6, wherein said converter is a video camera having logarithmic response characteristics.

9. The apparatus of claim 6, wherein said computer comprises a display and wherein said physical parameters are measured by displaying said electrical signal.

10. A method for correcting for the effect on image quality of a film processor which develops a radiographic image of a structure of interest on a film having an emulsion, comprising the steps of:

shielding a first portion of the film along one edge of the film from x-ray energy used for imaging of the structure of interest, which edge is furthest from the structure of interest;

impressing a first calibrated test pattern on the first portion of the film, said first pattern comprising a first calibrated graded stepwise density pattern having density positions, said density pattern produced by visible light, and a first plurality of symbols, located adjacent said first calibrated graded density pattern, wherein each symbol indicates the magnitude of one of said density positions;

providing a control film of similar emulsion as the emulsion of said film;

impressing a second calibrated test pattern along one edge of said control film said second calibrated test pattern comprising a second calibrated graded stepwise density pattern having density positions, said density pattern produced by visible light, and a second plurality of symbols, located adjacent said second calibrated graded density pattern, wherein each symbol indicates the magnitude of one of said density positions, wherein the intensity and spectrum of the visible light used for impressing said first calibrated test pattern and second test pattern are adjustable;

processing the film in a film processor to develop the first calibrated test pattern on the first portion of the film and the radiographic image of the structure of interest on the second portion of the film;

processing said control film to develop the second calibrated test pattern;

measuring the performance of the film processor used to develop the film by comparing and noting the symbols associated with those density positions between the first calibrated test pattern on the film and the second calibrated test pattern on the control film which match;

measuring physical parameters of selected portions of the developed image of the structure of interest, said parameters defining image quality; and correcting for the effect of film processor performance on said image quality by adjusting the values of said measured physical parameters according to the optical density values at the match positions of the first and second calibrated test patterns.

11. The method recited in claim 10 further comprising the step of coding the film to identify the film processor.

12. The method recited in claim 11 further comprising the step of coding the film to identify the facility that uses the processor.

13. The method recited in claim 12 further comprising the step of coding the film on the first portion to record the date on which the radiographic image was developed.

14. The method recited in claim 13 wherein the coding step is a photographic coding step.

15. The method recited in claim 10 wherein the second calibrated density pattern is precalibrated in terms of a plurality of parameters.

16. The method recited in claim 15 wherein the plurality of parameters is determined by densitometric analysis.

17. The method recited in claim 16 further comprising the step of identifying the film type and the control film type.

18. The method recited in claim 17 wherein the identifying step further comprises the steps of:

comparing a first means for identifying film type formed on the film with a second means for identifying film type formed on the control film to ensure that the film and control film are of similar emulsion.

19. The method recited in claim 18 wherein the radiographic image is an image of a mammography phantom.

20. The method recited in claim 17 wherein the first means for identifying film type and second means for identifying film type comprise at least one notch each oriented in a preferred direction.

21. The method recited in claim 10 wherein the procedure for quantifying and image parameters comprises:

illuminating said portions of said image with visible light of known intensity and spectrum;

optically adjusting the size of selected portions of the image;

imaging said selected portions of said image with a video camera, said camera having a logarithmic response; and digitizing said response for computer storage and manipulation.

22. A series of films for use in determining the effect on image quality of changes in film fog, speed or contrast resulting from changes in the performance of a film processor, said series of films comprising:

an imaging film, of a first emulsion, wherein said imaging film has been exposed to x-rays to image a structure of interest, said imaging film having been processed in said film processor;

a test film of a second emulsion, having a first calibrated test pattern impressed thereon, said first pattern comprising a first calibrated graded stepwise density pattern having density positions, said density pattern produced by visible light and a first plurality of symbols, located adjacent said first calibrated graded density pattern, wherein each symbol indicates the magnitude of one of said density positions, wherein said imaging film and said test film are developed in said film processor;

a control film, of a third emulsion, said control film containing calibrated test means, wherein said calibrated test means comprises a second calibrated graded density pattern produced by visible light and a second plurality of symbols located adjacent said second calibrated graded density pattern, wherein each symbol indicates the magnitude of a portion of said calibrated graded density pattern.

23. The films of claim 22, wherein said structure of interest comprises calibrated test objects for measuring film quality, said calibrated test objects comprising objects that are calibrated in terms of size, shape, thickness and composition, 24. The films of claim 22, wherein said first second and third emulsions are identical.

25. The films of claim 22, wherein the calibrated test means is impressed on the control film by visible light from a sensitometer.

26. The films of claim 22, further comprising at least one notch cut in the edge of said imaging film and in the edge of said control film said notch identifying the type of emulsion contained on said imaging and control films.

27. The films of claim 22, wherein the imaging film and the test film are processed simultaneously in the same film processor.

28. The films of claim 22, wherein the imaging film and the test film are processed sequentially in the same film processor.

29. The films of claim 22, wherein the imaging film and control film further comprise identification information.

30. A set of image quality standards for measuring image quality in mammography, comprising a plurality of objective measurements of physical parameters of a radiographic image of a breast phantom, said radiographic image being produced on a film of an emulsion, said emulsion having been developed in a film processor, wherein said objective measurements have been adjusted for the effect of the processor on said film.

31. A system for measuring image quality in mammography, said system comprising, a set of image quality standards developed in accordance with claim 30, a standardized breast phantom and a radiographic image of said breast phantom on which objective measurements of physical parameters on said radiographic image have been made, wherein said phantom is standardized according to measurements of radiographic images of artifacts contained within said phantom and wherein image quality is measured by comparing said test objective measurements with said standards.

32. A method of calibrating the image quality of a phantom wherein such phantom contains artifacts that differentially absorb-x-radiation, said method comprising the steps of:
    radiographing said phantom to create an x-ray image on a film composed of an emulsion;
    processing said film in a film processor to develop said image;
    illuminating a portion of said image with visible light of known intensity and spectrum;
    optically adjusting the size of selected portions of the image;
    imaging said selected portions of said image with a video camera, said camera having a logarithmic response;
    digitizing said response;
    providing a computer having stored therein data, said data describing control physical parameters of a control radiographic image of a control phantom;
    providing said digitized response to said computer;
    manipulating said digitized response in said computer in order to determine physical parameters corresponding to said control physical parameters; and
    calibrating the image quality of said x-ray image of said phantom in terms of the physical parameters determined by said computer from said x-ray images of said artifacts by comparing the determined physical parameters with said control physical parameters.

* * * * *